United States Patent [19]

Watanabe et al.

[11] Patent Number: 5,260,486

[45] Date of Patent: Nov. 9, 1993

[54] PROCESS FOR PRODUCING A BETA-KETOALCOHOL

[75] Inventors: Kazuhiro Watanabe; Eiji Nakanishi; Takayuki Suzuki; Kunisuke Izawa, all of Kawasaki, Japan

[73] Assignee: Ajinomoto Co., Inc., Tokyo, Japan

[21] Appl. No.: 924,480

[22] Filed: Aug. 4, 1992

[30] Foreign Application Priority Data

Aug. 15, 1991 [JP] Japan .................... 3-205259

[51] Int. Cl.$^5$ .............................. C07C 45/37
[52] U.S. Cl. .................... 568/311; 568/322; 568/306; 558/415
[58] Field of Search ............ 568/311, 322, 306; 558/415

[56] References Cited

U.S. PATENT DOCUMENTS 3,024,249   3/1962   Wöllner .................... 568/386

Primary Examiner—James H. Reamer
Attorney, Agent, or Firm—Oblon, Spivak, McClelland, Maier & Neustadt

[57] ABSTRACT

Herein is disclosed a process for producing a β-ketoalcohol by the oxidative ring-opening reaction of a 1,3-dioxane derivative, said β-ketoalcohol being able to be a substrate for asymmetric reaction.

6 Claims, No Drawings

PROCESS FOR PRODUCING A BETA-KETOALCOHOL

BACKGROUND OF THE INVENTION

1. Field of the Invention

β-Ketoalcohols are useful compounds as precursors for pharmaceuticals and specialty chemicals. For instance, a chiral 1,3-diol can be obtained by asymmetric reduction of a β-ketoalcohol, and positioned as an important intermediate for various optically active compounds.

The present invention concerns a process for producing a β-ketoalcohol.

A β-ketoalcohol is generally obtained easily by the aldol condensation of the corresponding ketone or aldehyde. With respect to primary alcohols out of β-ketoalcohols, however, no simple and inexpensive synthetic processes have been known yet. I.e., indeed there are for example, a method of selectively oxidizing one of the two hydroxyl groups of a diol (K.S. Kim et al., Synthesis, (11), 1017(1987)), and another method of reducing the corresponding ketocarboxylic acid (K. Isobe et al., Chem. Pharm. Bull., 34(7), 3029 (1986)), but such methods are complicated processes and are difficult to use industrially.

SUMMARY OF THE INVENTION

Accordingly, an object of the present invention is to develop an industrial process for producing a β-ketoalcohol including the above-mentioned primary alcohols conveniently and at a reduced cost The present invention thus provides a process for producing a β-ketoalcohol which process satisfies the above object of the present invention and other objects which will become apparent from the description of the invention herein below.

In an aspect of the present invention, there is provided a process for producing a β-ketoalcohol of the general formula (II):

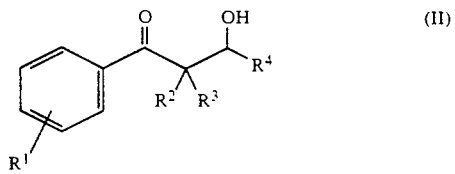

which process comprises reacting a 1,3-dioxane derivative of the general formula (I):

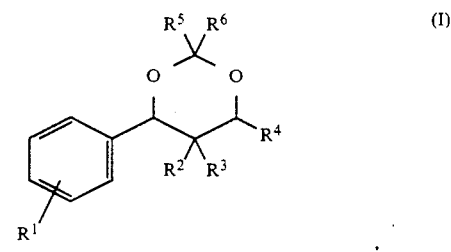

with an oxidizing agent. Preferred oxidizing agents are bromine, chlorine, an N-halogenoamide, an N-halogenoimide, a halogenous acid, and a hypohalogenous acid salt. They can be used together with hydrogen peroxide. A hydrogen halogenide when used together with hydrogen peroxide can be an oxidizing agent.

DETAILED DESCRIPTION OF THE INVENTION

The present inventors have made a profound study to attain the objects, and have, as a result, found that the objects can be attained by reacting a 1,3-dioxane derivative with an oxidizing agent, i.e., the oxidative ring-opening reaction of the 1,3-dioxane derivative. The present invention has been accomplished based on these findings.

That is, the present invention concerns a process for producing a β-ketoalcohol represented by the following general formula (II):

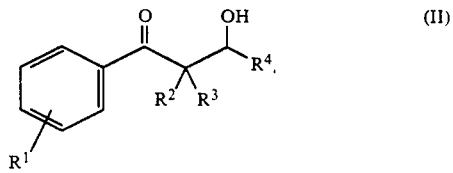

which process comprises reacting a 1,3-dioxane derivative represented by the following general formula (I):

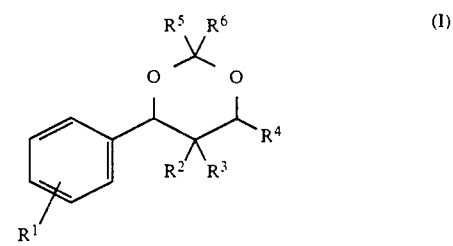

with an oxidizing agent.

In the above formulae, $R^1$, $R^2$, $R^3$, $R^4$, $R^5$ and $R^6$ each independently represent a hydrogen atom, a halogen atom, an alkyl group of 1 to 5 carbon atoms, an aryl group of 6 to 10 carbon atoms, a cycloalkyl group of 3 to 10 carbon atoms, or an aralkyl group of 7 to 20 carbon atoms. The alkyl, aryl, cycloalkyl and aralkyl groups may have substituent(s). Such substituents may be a halogen atom, a nitro group and cyano group.

1,3-Dioxane derivative as a starting material according to the present invention can be obtained easily from a styrene derivative by using a method as described, for example, by R.L. Shriner et al, in "Organic Synthesis Collective Volume 4, 786 (John Wiley & Sons, Inc.)".

As the oxidizing agent, there can be used, for example, bromine; chlorine; N-halogenoamides such as N-bromoacetoamide and N-chloroacetoamide; N-halogenoimides such as N-bromosuccinimide, N-chlorosuccinimide, N-bromophthalimide and N-chlorophthalimide; hypohalogenous acids such hypochlorous acid and hypobromous acid; and hypohalogenous acid salts such as sodium hypochlorite and sodium hypobromite. They can be used together with hydrogen peroxide. A hydrogen halogenide such as hydrogen bromide can be an oxidizing agent when used together with hydrogen peroxide.

Such oxidizing agents are used in an amount of from 0.5 to 2.0 equivalent per one equivalent of a 1,3-dioxane derivative of the formula (I). It is desirable that the amount of the oxidizing agent used is properly increased or decreased depending on the case since the reaction rate generally varies greatly depending on the kinds of the solvent and the derivative of the formula (I). If the amount of the oxidizing agent is insufficient, the reaction does not proceed sufficiently and, on the contrary, if the amount of the oxidizing agent is excessive, some side reactions take place undesirably.

There is no particular restriction on the reaction temperature. The reaction is generally carried out at $-10°$ to $40°$ C., while the reaction time is generally from several tens of minutes to several hours.

As the solvent for the reaction, there can be used, for example, halogen-containing organic solvents such as dichloromethane, chloroform, carbon tetrachloride, 1,2-dichloroethane and 1,1,1-trichloroethane; alcoholic organic solvents such as methanol, ethanol and isopropanol; ketone type organic solvents such as acetone and methyl ethyl ketone; ether type organic solvents such as tetrahydrofuran, diethyl ether and dioxane; aromatic organic solvents such as toluene and xylene; water; or a mixed solvent thereof; a mixed solvent of an organic solvent and water being used preferably.

The reaction conditions according to the present invention are not restricted only to the above, but the objects can be attained by properly selecting the reaction conditions depending on the reaction reagent and the solvent.

After the completion of the reaction, the desired product, i.e., $\beta$-ketoalcohol, can be separated and purified conventionally. E.g., it is separated from the reaction mixture by extracting with an organic solvent such as dichloromethane and purified by silica gel colum chromatography or distillation.

$\beta$-Ketoalcohols obtained according to the present invention can be converted into a corresponding (S) or (R) 1,3-diol having an asymmetric carbon atom by chemical asymmetric reduction (see T. Mukaiyama et al., Chemistry Letters, 1359 (1985)) or bacterial asymmetric reduction (see Japanese Patent Applications Nos. 299131/1991, 22466/1992 and 30782/1992).

EXAMPLE

Synthesis of 4-phenyl-1,3-dioxane, 4-(4'-methylphenyl)-1,3-dioxane, 4-(4'-chlorophenyl)-1,3-dioxane and 5-methyl-4-phenyl-1,3-dioxane, all used in the following examples, was carried out by the method as described by R.L. Shriner et al. in Organic Synthesis Collection Volume 4, 786 (John Wiley & Sons, Inc.).

EXAMPLE 1: PRODUCTION OF 3-HYDROXY-1-PHENYLPROPAN-1-ONE 0.82 g of 4-phenyl-1,3-dioxane was dissolved in 5 ml of dichloromethane. To the solution was added 5 ml of water. Then, the mixture was cooled to 5° C. 0.29 ml of bromine was added to the solution and allowed to react for 2 hours.

After completion of the reaction, the resulting reaction mixture was added with 10 ml of saturated aqueous solution of sodium sulfite, and extracted twice with 10 ml of dichloromethane. The dichloromethane layer was washed with saturated aqueous solution of sodium chloride, dried over anhydrous sodium sulfate, and then concentrated. The residue was purified by silica gel column chromatography, to obtain 0.53 g of the above-captioned compound (yield, 70.6%).

$^1$H-NMR (300 MHz, CDCl$_3$) $\delta$ : 2.66 (t, J=6.6Hz, 1H, —OH), 3.24 (t, J=5.3Hz, 2H), 4.04 (dt, J=5.3Hz, 6.6Hz, 2H), 7.4–7.5 (m, 2H), 7.5–7.6 (m, 1H), 7.9–8.0 (m, 2H).

Mass Spectra (FAB) : 151 (MH$^+$).

Boiling Point : 114.5°–115° C. (0.95–1.0 mmHg).

EXAMPLE 2: PRODUCTION OF 3-HYDROXY-1-PHENYLPROPAN-1-ONE 0.82 g of 4-phenyl-1,3-dioxane was dissolved in a mixed solvent of 40 ml of diethyl ether, 7 ml of methanol and 7 ml of water. To the solution were added 2.07 g of N-bromo-acetoamide and a catalytic amount of azobisisobutyronitrile. The mixture was refluxed under heating for four hours.

After completion of the reaction, the reaction mixture was added with 20 ml of saturated aqueous solution of sodium sulfite, and then extracted twice with 20 ml of dichloromethane. The dichloromethane layer was washed with saturated aqueous solution of sodium chloride, dried over anhydrous sodium sulfate, and then concentrated. The residue was purified by silica gel column chromatography, to obtain 0.55 g of the above-captioned compound (yield, 73.3%).

$^1$H-NMR (300 MHz, CDCl$_3$) $\delta$ : 2.66 (t, J=6.6Hz, 1H, —OH), 3.24 (t, J=5.3 Hz, 2H), 4.04 (dt, J=5.3Hz, 6.6Hz, 2H), 7.4–7.5 (m, 2H), 7.5–7.6 (m, 1H), 7.9–8.0 (m, 2H).

Mass Spectra (FAB) : 151 (MH+).

EXAMPLE 3: PRODUCTION OF 3-HYDROXY-1-(4'-METHYLPHENYL)PROPAN-1-ONE 1.00 g of 4-(4'-methylphenyl)-1,3-dioxane was dissolved in 6 ml of dichloromethane, and was added with 4ml of water. The mixture was cooled to 4° C. 0.32 ml of bromine was added to the solution and allowed to react for 2.5 hours.

After completion of the reaction, the resulting reaction mixture was added with 10 ml of saturated aqueous solution of sodium sulfite, and then extracted twice with 10 ml of dichloromethane. The dichloromethane layer was washed with saturated aqueous solution of sodium hydrogen carbonate and then saturated aqueous solution of sodium chloride, dried over anhydrous sodium sulfate, and then concentrated. The residue was purified by silica gel column chromatography, to obtain 0.46 g of the above-captioned compound (yield, 49.9%).

$^1$H-NMR (300 MHz, CDCl$_3$) $\delta$ : 2.42 (s, 3H), 2.70 (t, J=6.7Hz, 1H, —OH), 3.21 (t, J=5.3Hz, 2H), 4.03 (dt, J=5.3Hz, 6.7Hz, 2H), 7.2–7.3 (m, 2H), 7.8–7.9 (m, 2H).

Mass Spectra (FAB) : 165 (MH+).

EXAMPLE 4: PRODUCTION OF 1-(4'-CHLOROPHENYL)-3-HYDROXY-PROPAN-1-one 329 mg of 4-(4'-chlorophenyl)-1,3-dioxane was dissolved in 1.5 ml of dichloromethane, and was added with 1 ml of water. The mixture was cooled in an ice bath. The solution was added with 0.10 ml of bromine and allowed to react for 2 hours and 30 minutes.

After completion of the reaction, the resulting reaction mixture was added with 5 ml of saturated aqueous solution of sodium sulfite, and then extracted twice with 5 ml of dichloromethane. The dichloromethane layer was washed with saturated aqueous solution of sodium hydrogen carbonate and then saturated aqueous solution of sodium chloride, dried over anhydrous sodium sulfate, and then concentrated. The residue was purified by silica gel column chromatography, to obtain 225 mg of the above-captioned compound (yield, 73.4%).

$^1$H-NMR (300 MHz, CDCl$_3$) δ : 2.55 (t, J=6.6Hz, 1H, —OH), 3.20 (t, J=5.3Hz, 2H), 4.03 (dt, J=5.3Hz, 6.6Hz, 2H), 7.4–7.5 (m, 2H), 7.8–7.9 (m, 2H).

Mass Spectra (FAB) : 185 (MH+).

EXAMPLE 5: PRODUCTION OF 3-HYDROXY-2-METHYL-1-PHENYLPROPAN-1-ONE 509 mg of 5-methyl-4-phenyl-1,3-dioxane was dissolved in 3 ml of dichloromethane, and was added with 2 ml of water. The mixture was cooled in an ice bath. The solution was added with 0.16 ml of bromine and allowed to react for 2 hours and 30 minutes.

After completion of the reaction, the resulting reaction mixture was added with 10 ml of saturated aqueous solution of sodium sulfite, and then extracted twice with 10 ml of dichloromethane. The dichloromethane layer was washed with saturated aqueous solution of sodium hydrogen carbonate and then saturated aqueous solution of sodium chloride, dried over anhydrous sodium sulfate, and then concentrated. The residue was purified by silica gel column chromatography, to obtain 239 mg of the above-captioned compound (yield, 51.0%).

$^1$H-NMR (300 MHz, CDCl$_3$) δ : 1.25 (d, J=7.3Hz, 3H), 2.32 (br. t, 1H, —OH), 3.68 (ddq, J=4.2Hz, 7.3Hz, 7.3 Hz, 1H), 3.82 (ddd, J=4.2Hz, 6.3Hz, 10.8Hz, 1H), 3.94 (ddd, J=7.3Hz, 7.3Hz, 10.8Hz, 1H), 7.4–7.5 (m, 2H), 7.5–7.6 (m, 1H), 7.9–8.0 (m, 2H).

Mass Spectra (FAB) : 165 (MH+).

EXAMPLE 6: PRODUCTION OF 3-HYDROXY-1-PHENYLPROPANE-1-ONE 100 g of 4-phenyl-1,3-dioxane was dissolved in 488 ml of dichloromethane, and was added with 285 ml of water and 126 ml of 30% aqueous hydrogen peroxide. The solution was heated to 30° C. 11 ml of bromine was added to the solution and the mixture was allowed to react for 4.5 hours at 30° C.

After completion of the reaction, 300 ml of saturated aqueous solution of sodium sulfite was added to the resulting reaction mixture, and the mixture was extracted with dichloromethane (2×100 ml). The dichloromethane layer was washed with saturated aqueous solution of sodium hydrogen carbonate. To the dichloromethane layer was added 300 ml of water and 100 ml of 27% aqueous ammonia, and the mixture was stirred for 3 hours. The resulting mixture was partitioned and the aqueous layer was extracted with dichloromethane (70 ml ×2). The combined dichloromethane layer was washed with saturated aqueous solution of sodium chloride, and dried over anhydrous sodium sulfate. The solution was concentrated and 87.40 g of the above-captioned compound (purity, 94.2%; yield, 90.0% ) was obtained.

EXAMPLE 7: PRODUCTION OF 3-HYDROXY-1-PHENYLPROPANE-1-ONE

To a dichloromethane (24 ml) solution of 5.00 g of 4-phenyl-1,3-dioxane was added 11 of water and 9.3 ml of 30% aqueous hydrogen peroxide. To this solution, 2.1 g of 47% hydrobromic acid was added, and stirring was continued for 2.5 hours at room temperature.

After completion of the reaction, the resulting reaction mixture was added with 30 ml of saturated aqueous solution of sodium sulfite and extracted with dichloromethane (15 ml ×2). The dichloromethane layer was washed with saturated aqueous solution of sodium hydrogen carbonate and then saturated aqueous solution of sodium chloride, and dried over anhydrous sodium sulfate. This solution was concentrated to afford 4.6 g of the above-captioned compound (purity, 81.8%; yield, 82.3%).

What is claimed is:

1. A process for producing a β-ketoalcohol represented by the following general formula (II):

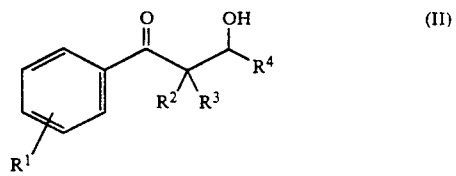

in which R$^1$, R$^2$, R$^3$, and R$^4$ each independently represent a hydrogen atom, a halogen atom, an alkyl group of 1 to 5 carbon atoms, an aryl group of 6 to 10 carbon atoms, a cycloalkyl group of 3 to 10 carbon atoms, or an aralkyl group of 7 to 20 carbon atoms; wherein said alkyl, aryl, cycloalkyl, and aralkyl groups may be substituted with a halogen, a nitro group, or a cyano group;

which process comprises reacting a dioxane derivative represented by the following general formula (I):

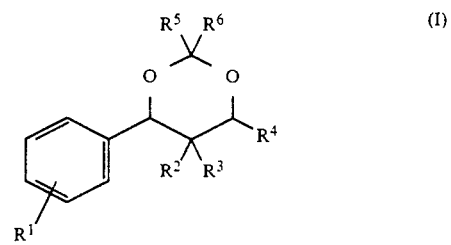

in which R$^1$, R$^2$, R$^3$, R$^4$, R$^5$ and R$^6$ each independently represent a hydrogen atom, a halogen atom, alkyl group of 1 to 5 carbon atoms, aryl group of 6 to 10 carbon atoms, cycloalkyl group of 3 to 10 carbon atoms, or aralkyl group of 7 to 20 carbon atoms, wherein said alkyl, aryl, cycloalkyl, and aralkyl groups, may be substituted with a halogen, a nitro group, or a cyano group;

with an oxidizing agent, wherein said reaction is conducted in a solvent selected from the group consisting of a halogen-containing organic, alcoholic organic, ketone type organic, ether type organic, aromatic organic, aqueous, or mixture thereof, at a temperature and time suitable to effect oxidation.

2. The process as defined in claim 3, wherein said oxidizing agent is bromine, chlorine, an N-halogenoamide, an N-halogenoimide, a hypochalogenous acid, a hyophalogenous acid salt or a hydrogen halogenide, which oxidizing agent can be used together with hydrogen peroxide.

3. The process according to claim 1, wherein said solvent is selected from the group consisting of: dichloromethane, chloroform, carbon tetrachloride, 1,2-dichloroethane, 1,1,1-trichloroethane, methanol, ethanol, isopropanol, acetone, methyl ethyl ketone, tetrahydrofuran, diethyl ether, dioxane, toluene, xylene, water, and mixtures thereof.

4. The process to claim 1, wherein said solvent is preferably a mixed solvent of an organic solvent and water.

5. The process according to claim 1, wherein said temperature is −10° to 40° C.

6. The process according to claim 1, wherein said oxidizing agent is used in an amount of from 0.5 to 2.0 equivalents per 1 equivalent of said dioxane derivative (I).

* * * * *

UNITED STATES PATENT AND TRADEMARK OFFICE
CERTIFICATE OF CORRECTION

PATENT NO. : 5,260,486

DATED : November 9, 1993

INVENTOR(S) : Kazuhiro Watanabe, et al

It is certified that error appears in the above-indentified patent and that said Letters Patent is hereby corrected as shown below:

Column 6, line 56 "in claim 3," should read  --in claim 1,--.

Signed and Sealed this

Twenty-seventh Day of September, 1994

Attest:

BRUCE LEHMAN

Attesting Officer    Commissioner of Patents and Trademarks